(12) United States Patent
Crear et al.

(10) Patent No.: US 10,814,391 B2
(45) Date of Patent: Oct. 27, 2020

(54) ADDITIVE MANUFACTURING MATERIAL ANALYSIS SYSTEM AND RELATED METHOD

(71) Applicant: General Electric Company, Schenectady, NY (US)

(72) Inventors: Donnell Eugene Crear, Simpsonville, SC (US); Ray Joshua Bohon, Campobello, SC (US); Steven Charles Woods, Easley, SC (US)

(73) Assignee: General Electric Company, Schenectady, NY (US)

( * ) Notice: Subject to any disclaimer, the term of this patent is extended or adjusted under 35 U.S.C. 154(b) by 332 days.

(21) Appl. No.: 15/263,989

(22) Filed: Sep. 13, 2016

(65) Prior Publication Data

US 2018/0071821 A1    Mar. 15, 2018

(51) Int. Cl.
| | |
|---|---|
| *B29C 67/00* | (2017.01) |
| *B22F 3/105* | (2006.01) |
| *B29C 64/393* | (2017.01) |
| *B22F 3/00* | (2006.01) |
| *B33Y 30/00* | (2015.01) |
| *B33Y 50/02* | (2015.01) |
| *B23K 26/342* | (2014.01) |
| *G01N 1/10* | (2006.01) |
| *G01N 33/00* | (2006.01) |

(52) U.S. Cl.
CPC ............ *B22F 3/1055* (2013.01); *B22F 3/003* (2013.01); *B22F 3/008* (2013.01); *B23K 26/342* (2015.10); *B29C 64/393* (2017.08); *B33Y 30/00* (2014.12); *B33Y 50/02* (2014.12); *G01N 1/10* (2013.01); *G01N 33/00* (2013.01); *B22F 2003/1056* (2013.01); *B22F 2003/1057* (2013.01); *G01N 2033/0091* (2013.01); *Y02P 10/25* (2015.11)

(58) Field of Classification Search
CPC ..... B29C 64/00; B29C 64/112; B29C 64/268; B29C 64/386; B29C 64/393; B33Y 10/00; B33Y 50/00
USPC .......................... 700/98, 117, 118, 119, 120
See application file for complete search history.

(56) References Cited

U.S. PATENT DOCUMENTS 8,260,447 B2    9/2012 Mattes et al.
9,031,680 B2 *  5/2015 Napadensky ......... B29C 64/106
                                                     264/401

(Continued)

FOREIGN PATENT DOCUMENTS

| WO | 2015025171 A2 | 2/2015 |
| WO | 2015112726 A1 | 7/2015 |

*Primary Examiner* — Thu Khanh T Nguyen
(74) *Attorney, Agent, or Firm* — James Pemrick; Hoffman Warnick LLC

(57) ABSTRACT

Various aspects include systems and methods for analyzing materials in additive manufacturing processes. In some cases, a system includes: an additive manufacturing (AM) printer for printing an AM object, the AM printer including a raw material chamber and a build chamber; a control system coupled with the AM printer configured to control the printing of the AM object; and a material analysis system coupled with the control system and the AM printer, the material analysis system configured to analyze a raw material obtained directly from at least one of the raw material chamber or the build chamber for a defect prior to, or contemporaneously with, additively manufacturing the AM component.

19 Claims, 2 Drawing Sheets

(56) References Cited

U.S. PATENT DOCUMENTS

| | | | |
|---|---|---|---|
| 9,482,974 B2* | 11/2016 | Martin | B33Y 10/00 |
| 2008/0258330 A1* | 10/2008 | Muller | B29C 64/153 |
| | | | 264/113 |
| 2015/0034606 A1 | 2/2015 | Blackmore | |
| 2015/0177158 A1 | 6/2015 | Cheverton | |
| 2015/0266211 A1 | 9/2015 | Wolfgang et al. | |
| 2015/0266236 A1 | 9/2015 | Farah et al. | |
| 2015/0283610 A1 | 10/2015 | Ljunglad et al. | |
| 2015/0328839 A1* | 11/2015 | Willis | G05B 19/4099 |
| | | | 700/98 |
| 2016/0054205 A1 | 2/2016 | O'Neill | |
| 2016/0067779 A1 | 3/2016 | Dautova et al. | |
| 2016/0193696 A1* | 7/2016 | McFarland | B29C 64/357 |
| | | | 219/76.12 |
| 2017/0050382 A1* | 2/2017 | Minardi | B33Y 50/02 |
| 2017/0334134 A1* | 11/2017 | Herzog | B29C 64/153 |

* cited by examiner

ADDITIVE MANUFACTURING MATERIAL ANALYSIS SYSTEM AND RELATED METHOD

BACKGROUND

The subject matter disclosed herein relates to the manufacture of components. Specifically, the subject matter disclosed herein relates to systems for managing materials in additive manufacturing.

Additive manufacturing is an increasingly prevalent approach for fabricating components in various sectors, including the industrial sector. Additive manufacturing processes can reduce design cycle time and material waste, and may provide for greater flexibility in fabricating custom components. However, many conventional approaches fail to adequately control the quality of additive manufacturing products, including the materials used during additive manufacturing processes.

BRIEF DESCRIPTION

Various aspects of the disclosure include systems and methods for analyzing materials in additive manufacturing processes. In some cases, a system includes: an additive manufacturing (AM) printer for printing an AM object, the AM printer including a raw material chamber and a build chamber; a control system coupled with the AM printer configured to control the printing of the AM object; and a material analysis system coupled with the control system and the AM printer, the material analysis system configured to analyze a raw material obtained directly from at least one of the raw material chamber or the build chamber for a defect prior to, or contemporaneously with, additively manufacturing the AM component.

A first aspect of the disclosure includes a system having: an additive manufacturing (AM) printer for printing an AM object, the AM printer including a raw material chamber and a build chamber; a material analysis system coupled with the AM printer, the material analysis system configured to: sample a raw material for manufacturing the AM object from at least one of the raw material chamber or the build chamber; and a control system coupled with the AM printer and the material analysis system, the control system configured to control the printing of the AM object, wherein at least one of the material analysis system or the control system is configured to compare at least one characteristic of the raw material to a threshold characteristic range, and wherein the control system is further configured to modify at least one of object code defining the AM object or instructions to the AM printer for manufacturing the AM object in response to the at least one characteristic deviating from the threshold characteristic range.

A second aspect of the disclosure includes a method including: sampling a raw material for manufacturing an additively manufactured (AM) object from at least one of a raw material chamber or a build chamber in an AM printer; comparing at least one characteristic of the raw material to a threshold characteristic range; and modifying at least one of object code defining the AM object or instructions to the AM printer for manufacturing the AM object in response to the at least one characteristic deviating from the threshold characteristic range.

A third aspect of the disclosure includes a system having: an additive manufacturing (AM) printer for printing an AM object, the AM printer including a raw material chamber and a build chamber; a control system coupled with the AM printer configured to control the printing of the AM object; and a material analysis system coupled with the control system and the AM printer, the material analysis system configured to analyze a raw material obtained directly from at least one of the raw material chamber or the build chamber for a defect prior to, or contemporaneously with, additively manufacturing the AM component.

BRIEF DESCRIPTION OF THE DRAWINGS

These and other features of this invention will be more readily understood from the following detailed description of the various aspects of the invention taken in conjunction with the accompanying drawings that depict various embodiments of the disclosure, in which.

Figure 1:
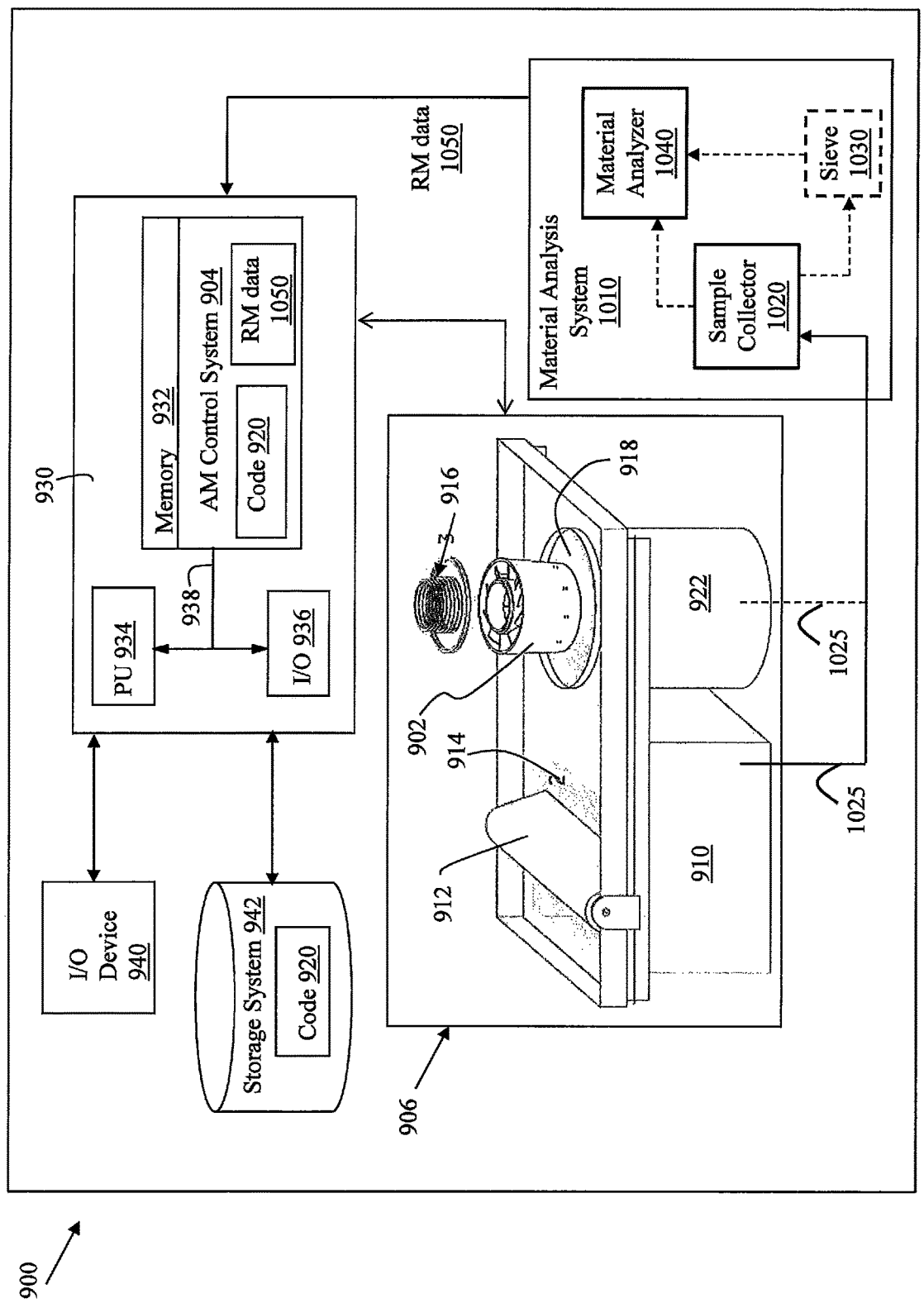
FIG. 1 shows a schematic depiction of an additive manufacturing system according to various embodiments of the disclosure.

It is noted that the drawings of the invention are not necessarily to scale. The drawings are intended to depict only typical aspects of the invention, and therefore should not be considered as limiting the scope of the invention. In the drawings, like numbering represents like elements between the drawings.

DETAILED DESCRIPTION

The subject matter disclosed herein relates to the manufacture of components. Specifically, the subject matter disclosed herein relates to systems for monitoring materials used in additive manufacturing.

As noted herein, conventional additive manufacturing systems do not adequately analyze their manufactured products. Many conventional additive manufacturing processes involve analyzing the product after it has been manufactured, or analyzing the excess material (e.g., powder, such as polymer or plastic powder) used to form the product after the part has been manufactured. Because the material (e.g., powder) is affected by the additive manufacturing process, these conventional approaches fail to adequately characterize the material as it is used to manufacture the product. For example, the gas content (e.g., oxygen content, nitrogen content, etc.) and/or consistency of that powder, prior to manufacture, is not measured in the conventional approaches. This can make it difficult to determine whether any defects in the manufactured product are caused by manufacturing processes, product design, or underlying material (e.g., powder).

According to various embodiments of the disclosure, in contrast to conventional approaches, systems described herein are configured to continuously sample powder from an (additive manufacturing system) feed hopper or reservoir prior to (or contemporaneously with) administration of that powder to the build platform. That is, these systems include a material (e.g., powder) analyzer positioned to sample additive manufacturing powder prior (e.g., immediately or near-immediately prior) to employing that powder in an additive manufacturing process, or during the manufacturing process. These systems can improve the additive manufacturing process, for example, by allowing for characterization of the material (e.g., powder) used to form components, prior to formation (e.g., during formation process or prior to initiation of the process).

As used herein, additive manufacturing (AM) may include any process of producing an object through the successive layering of material rather than the removal of material, which is the case with conventional processes. Additive manufacturing can create complex geometries without the use of any sort of tools, molds or fixtures, and with little or no waste material. Instead of machining components from solid billets of material (e.g., plastic), much of which is cut away and discarded, the only material used in additive manufacturing is what is required to shape the part. Additive manufacturing processes may include but are not limited to: 3D printing, rapid prototyping (RP), direct digital manufacturing (DDM), selective laser melting (SLM) and direct metal laser melting (DMLM).

Turning to FIG. 1, an additive manufacturing system 900 for generating an object (or product) 902 is shown according to various embodiments of the disclosure. In various embodiments, system 900 is arranged for DMLM. However, it is understood that the general teachings of the disclosure are equally applicable to other forms of additive manufacturing. Object 902 is illustrated as a double walled turbine element; however, it is understood that the additive manufacturing process can be readily adapted to manufacture any number of different objects. AM system 900 can include a computerized additive manufacturing (AM) control system 904 coupled with (e.g., wirelessly connected with and/or hard-wired with) an AM printer 906. According to various embodiments, AM system 900, as will be described, executes code 920 that includes a set of computer-executable instructions defining object 902 to physically generate the object 902 using AM printer 906. Each AM process may use different raw materials in the form of, for example, fine-grain powder, liquid (e.g., polymers), sheet, etc., a stock of which may be held in a chamber 910 of AM printer 906. In one example embodiment, object 902 may be made of metal or alloy materials, and chamber 910 can include a raw material, e.g., a powder, for forming object 902. As illustrated, in various embodiments, an applicator 912 may create a thin layer of raw material 914 spread out as the blank canvas from which each successive slice of the final object will be created. In other cases, applicator 912 may directly apply or print the next layer onto a previous layer as defined by code 920, e.g., where the material is a metal. In the example shown, a laser or electron beam 916 fuses particles for each slice, as defined by code 920. Various parts of AM printer 906 may move to accommodate the addition of each new layer, e.g., a build platform 918 may lower (within a build chamber 922 for containing object 902) and/or chamber 910 and/or applicator 912 may rise after each layer.

AM control system 904 is shown implemented on computer 930 as computer program code. To this extent, computer 930 is shown including a memory 932, a processor 934, an input/output (I/O) interface 936, and a bus 938. Further, computer 930 is shown in communication with an external I/O device/resource 940 and a storage system 942. In general, processor 934 executes computer program code, such as AM control system 904, that is stored in memory 932 and/or storage system 942 under instructions from code 920 representative of object 902, described herein. While executing computer program code, processor 934 can read and/or write data to/from memory 932, storage system 942, I/O device 940 and/or AM printer 906. Bus 938 provides a communication link between each of the components in computer 930, and I/O device 940 can comprise any device that enables a user to interact with computer 940 (e.g., keyboard, pointing device, display, etc.). Computer 930 is only representative of various possible combinations of hardware and software. For example, processor 934 may comprise a single processing unit, or be distributed across one or more processing units in one or more locations, e.g., on a client and server. Similarly, memory 932 and/or storage system 942 may reside at one or more physical locations. Memory 932 and/or storage system 942 can comprise any combination of various types of non-transitory computer readable storage medium including magnetic media, optical media, random access memory (RAM), read only memory (ROM), etc. Computer 930 can comprise any type of computing device such as a network server, a desktop computer, a laptop, a handheld device, a mobile phone, a pager, a personal data assistant, etc.

Additive manufacturing processes begin with a non-transitory computer readable storage medium (e.g., memory 932, storage system 942, etc.) storing code 920 representative of object 902. As noted, code 920 includes a set of computer-executable instructions defining object 902, upon execution of code 920 by system 900. For example, code 920 may include a precisely defined 3D model of AM object 902 and can be generated from any of a large variety of well-known computer aided design (CAD) software systems such as AutoCAD®, TurboCAD®, DesignCAD 3D Max, etc. In this regard, code 920 can take any now known or later developed file format. For example, code 920 may be in the Standard Tessellation Language (STL) which was created for stereolithography CAD programs of 3D Systems, or an additive manufacturing file (AMF), which is an American Society of Mechanical Engineers (ASME) standard that is an extensible markup-language (XML) based format designed to allow any CAD software to describe the shape and composition of any three-dimensional object to be fabricated on any AM printer. Code 920 may be translated between different formats, converted into a set of data signals and transmitted, received as a set of data signals and converted to code, stored, etc., as necessary. Code 920 may be an input to system 900 and may come from a part designer, an intellectual property (IP) provider, a design company, the operator or owner of system 900, or from other sources. In any event, AM control system 904 executes code 920, dividing object 902 into a series of thin slices that it assembles using AM printer 906 in successive layers of liquid, powder, sheet or other material. In the DMLM example, each layer is melted to the exact geometry defined by code 920 and fused to the preceding layer. Subsequently, the object 902 may be exposed to any variety of finishing processes, e.g., minor machining, sealing, polishing, assembly to other part of the igniter tip, etc.

According to various embodiments, system 900 further includes a material analysis system 1010 configured to analyze the raw material 914 (e.g., powder) stored in chamber 910 at a time nearly preceding or immediately preceding deployment of that material 914 by applicator 912. In other embodiments, material analysis system 1010 can be configured to analyze the raw material 914 during the build process, e.g., while within build chamber 922. In further embodiments, material analysis system 1010 can be configured to analyze the raw material 914 that is collected during the build process (e.g., throughout the build process), at a later time (e.g., after conclusion of the build process).

Material analysis system 1010 can include a sample collector 1020 coupled with (e.g., fluidly coupled or otherwise coupled to access raw material 914 within) chamber 910 for obtaining a sample of raw material 914 (e.g., powder), e.g., via one or more conduits 1025. Sample collector 1020 can include a conduit, cartridge, and/or other enclosure capable of receiving raw material 914 and, in some cases, storing raw material 914 prior to analysis. In some cases, where raw material 914 includes a powder, material analysis system 1010 can further include a sieve 1030 coupled with (e.g., fluidly coupled or otherwise coupled to access raw material 914 within) sample collector 1020. Sieve 1030 can include a conventional sieve device for straining particulate, such as powder or flowable solids. In some cases, where raw material 914 does not include a powder, sieve 1030 may be optional (as shown in dashed lines in FIG. 1). In any case, material analysis system 1010 can further include a material analyzer 1040, coupled with (e.g., fluidly coupled or otherwise coupled to access raw material 914 within) sample collector 1020 (directly or indirectly), and in some cases, sieve 1030 (where sieve 1030 is located between sample collector 1020 and material analyzer 1040).

Material analyzer 1040 can include a plurality of sensors configured to measure at least one characteristic of raw material 914, including, for example: a shape and/or morphology of raw material 914, the density of raw material 914, the particle size distribution of raw material 914, the flow-ability of raw material 914, the moisture content of raw material 914 and/or the oxygen and nitrogen pickup of raw material 914. In various embodiments, material analyzer 1040 includes sensors such as flowmeter(s), rheometer(s), optical sensor(s), scale(s), piezoelectric sensor(s), moisture/humidity sensor(s), oxygen sensor(s), etc., for analyzing particular characteristics of raw material 914.

Material analysis system 1010, and in particular, material analyzer 1040, can be coupled (e.g., wirelessly and/or hard-wired) with computer 930, and in particular, AM control system 904. Material analyzer 1040 can provide raw material (RM) data 1050 to AM control system 904, for further analysis and/or modification of code 920 or other processes in AM printer 906, to improve manufacturing processes in forming object 902. In various other embodiments, material analyzer 1040 and/or AM control system 904 can include a data storage device or other memory device for storing threshold characteristic ranges for particular characteristics of raw material(s) 914. Material analyzer 1040 can further include processing components capable of comparing RM data 1050 with particular thresholds (e.g., threshold ranges). In these cases, material analyzer 1040 can provide RM data 1050 to control system 904, which indicates that raw material 914 deviates from one or more threshold ranges, or falls within one or more threshold ranges. In other cases, AM control system 904 compares RM data 1050 from material analyzer 1040 with particular thresholds (e.g., threshold ranges). In any case, system 900 has the technical effect of improving additive manufacturing processes relative to conventional systems, e.g., by improving analysis of raw materials 914 used in such processes.

Figure 2:
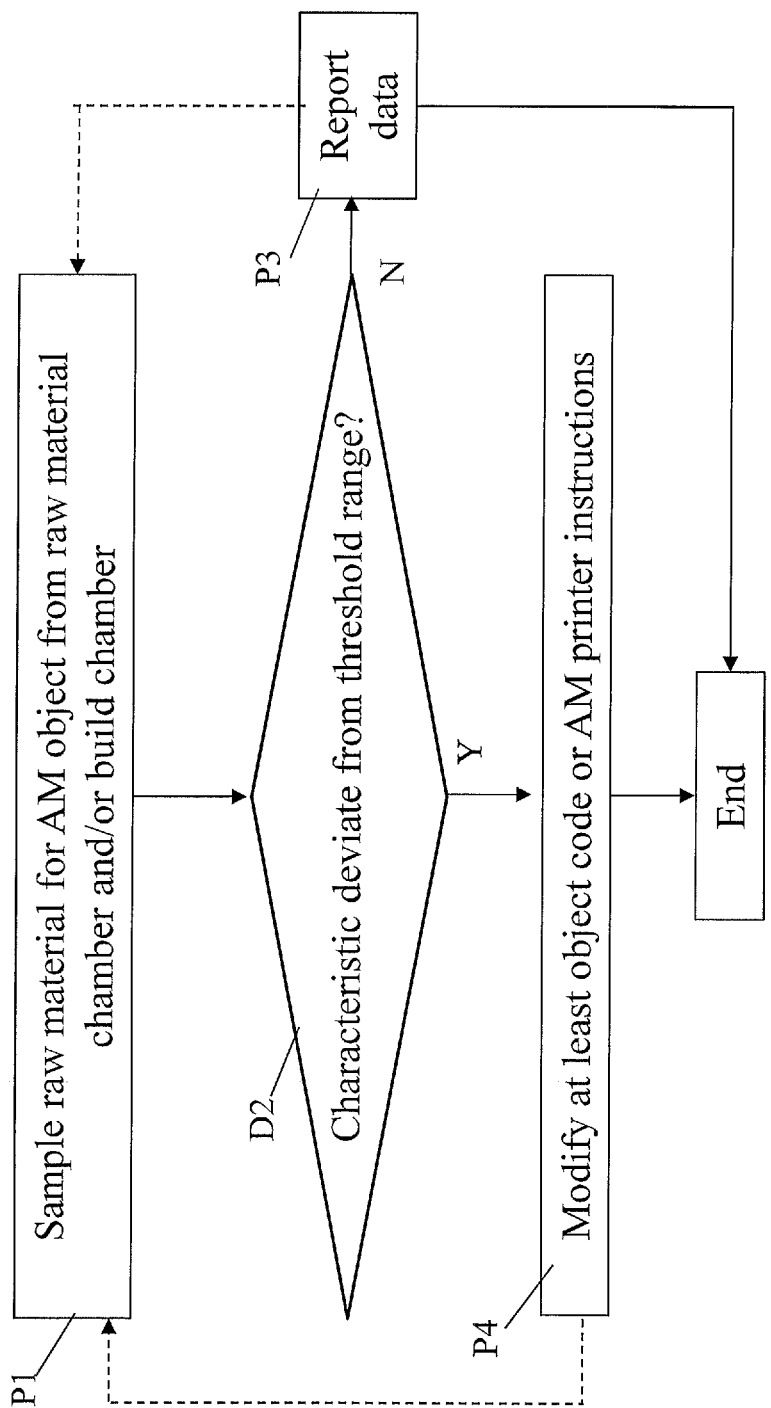
FIG. 2 shows a flow diagram illustrating processes according to various embodiments of the disclosure.

FIG. 2 is a flow diagram illustrating an example method performed according to various embodiments of the disclosure. In some cases, portions of the method are performed by material analysis system 1010 and/or AM control system 904. FIG. 2 is referred to simultaneously with the system diagram of FIG. 1. According to various embodiments, a method can include the following processes:

Process P1: sampling a raw material 914 for forming an additively manufactured AM object 902 from at least one of a raw material chamber 910 or a build chamber 922. This process can include obtaining the raw material 914 via one or more conduits 1025. In some cases, conduits 1025 can include a vacuum or valve system for drawing raw material 914 from raw material chamber 910 and/or build chamber 922 on demand. In various embodiments, material analysis system 1010, an in particular, sample collector 1020, can include an actuator or signaling device to initiate collection of raw material 914, e.g., via a vacuum, valve, etc. from raw material chamber 910 or build chamber 922. As described herein, sampling of raw material 914 is performed prior to manufacturing object 902, or contemporaneously with such manufacture, and in some particular cases, the sampling is performed within several (e.g., 4-6) minutes prior to additively manufacturing AM object 902. In some particular cases, raw material 914 is sampled during the build process, and analyzed immediately after the build process concludes.

Decision D2 (performed by at least one of AM control system 904 or material analysis system 1010): does a characteristic of raw material 914 deviate from a threshold characteristic range (e.g., include a defect)? In some cases, the characteristic(s) of raw material 914 can include at least one of a shape and/or morphology of raw material 914, the density of raw material 914, the particle size distribution of raw material 914, the flow-ability of raw material 914, the moisture content of raw material 914 and/or the oxygen pickup of raw material 914. In various embodiments, the characteristic of raw material 914 can have an acceptable value or range of values, which establish the threshold range. For example, based upon the type of raw material (e.g., powder) 914 and the code 920 defining object 902, a density threshold could be a defined density range (X g/cm3 to 3X g/cm3), while a moisture content threshold could be a defined upper bound, such as X volumetric water content or Z gravimetric volume content (plus/minus a measurement error), where X, Y, Z are values of particular characteristics. These thresholds could be pre-defined based upon code 920 defining object 902 (e.g., particular features of object 902, such as contours, thickness, etc.) and/or material 914 type (e.g., powder, liquid, etc.). In some cases, the thresholds are determined based upon a defect in object 902, or a known correlation with a defect in object 902 due to a characteristic in raw material 914. For instance, it may be known or discovered (e.g., via modelling or physical formation and analysis) that a particular object 902 is subject to a defect (e.g., mechanical failure, inadequate surface roughness, misalignment, etc.) at a contour, joint or other feature due at least in part to the characteristics of raw material 914 (e.g., moisture content, density, etc.).

Process P3: If No to decision D2, RM data 1050 is reported to AM control system 904, e.g., from material analysis system 1010 or data is otherwise stored, or made available for display via computer 930 (in the case that AM control system 904 performs Decision D2), and process ends (or repeats, as noted herein).

Process P4: If Yes to decision D2 (in response to characteristic of raw material 914 deviating from a threshold characteristic range), AM control system 904 modifies at least one of code 920 used to define AM object 902 or instructions to AM printer 906. This can include modifying code 920 to account for the particular characteristic(s) of raw material 914 (e.g., oxygen content, density, etc.), and/or modifying instructions to AM printer 906, such as increasing production speed where oxygen content is above a threshold characteristic range, or decreasing production speed where density is below a threshold range. In some cases, code 920 can be modified to increase or decrease a thickness of particular layers of AM object 902, modify angles of particular layer(s) of AM object 902, etc. In some cases, this process can include modifying instructions to AM printer 906 to utilize a distinct type of raw material 914, or can simply include modifying instructions to AM printer 906 to indicate a defect in the raw material 914.

It is understood that Processes P1-P4 (including Decision D2) can be repeated on demand, or continuously, according to any schedule.

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A system comprising:
    an additive manufacturing (AM) printer for printing an AM object, the AM printer including a raw material chamber and a build chamber;
    a material analysis system coupled with the AM printer, the material analysis system configured to:
        obtain a sample of a raw material for manufacturing the AM object from the raw material chamber, and
        analyze the obtained sample of the raw material to measure at least one characteristic of the raw material;
    a control system coupled with the AM printer and the material analysis system, the control system configured to control the printing of the AM object, the control system including object code defining the AM object and the object code includes instructions to the AM printer for manufacturing the AM object,
    wherein at least one of the material analysis system or the control system is configured to compare the at least one measured characteristic of the raw material to a threshold characteristic range, and
    wherein the control system is further configured to modify at least one of the object code defining the AM object and the object code includes the instructions to the AM printer for manufacturing the AM object in response to the at least one measured characteristic deviating from the threshold characteristic range; and
    a conduit directly connecting the raw material chamber with the material analysis system, the conduit configured to provide the obtained sample of the raw material from the raw material chamber to the material analysis system.

2. The system of claim 1, wherein the at least one measured characteristic includes at least one of: a shape of the raw material, a morphology of the raw material, a density of the raw material, a particle size distribution of the raw material, a flow-ability of the raw material, a moisture content of the raw material, or an oxygen pickup of the raw material.

3. The system of claim 1, wherein the material analysis system is further configured to report the at least one measured characteristic of the raw material to the control system in response to the at least one measured characteristic not deviating from the threshold characteristic range.

4. The system of claim 1, wherein the raw material includes a powder.

5. The system of claim 1, wherein the material analysis system is configured to obtain the sample of the raw material prior to or contemporaneously with the additively manufacturing of the AM object.

6. The system of claim 5, wherein the material analysis system is configured to obtain the sample of the raw material within several minutes prior to additively manufacturing the AM object.

7. The system of claim 1, wherein the material analysis system further comprises:
    a sample collector coupled with the conduit for collecting the obtained sample of the raw material from the raw material chamber;
    a sieve coupled with the sample collector for straining the obtained sample of the raw material; and
    a material analyzer coupled with the sieve for comparing the at least one measured characteristic of the raw material to the threshold characteristic range.

8. The system of claim 1, wherein the AM printer further includes an applicator coupled with the raw material chamber for applying the raw material to form the AM object, wherein the material analysis system is configured to sample the raw material prior to the raw material contacting the applicator to form the AM object.

9. A method comprising:
    obtaining a sample of a raw material for manufacturing an additively manufactured (AM) object from a raw material chamber in an AM printer, the sample of the raw material obtained via a conduit directly connecting the raw material chamber with a material analysis system;
    analyzing the obtained sample of the raw material to measure at least one characteristic of the raw material;
    comparing the at least one measured characteristic of the raw material to a threshold characteristic range; and
    modifying an object code defining the AM object of a control system and instructions in the control system, wherein the object code includes the instructions provided to the AM printer for manufacturing the AM object in response to the at least one measured characteristic deviating from the threshold characteristic range.

10. The method of claim 9, wherein the at least one measured characteristic includes at least one of: a shape of the raw material, a morphology of the raw material, a density of the raw material, a particle size distribution of the raw material, a flow-ability of the raw material, a moisture content of the raw material, or an oxygen pickup of the raw material.

11. The method of claim 9, further comprising reporting the at least one measured characteristic of the raw material in response to the at least one measured characteristic not deviating from the threshold characteristic range.

12. The method of claim 9, wherein the raw material includes a powder.

13. The method of claim 9, wherein the obtaining of the sample of the raw material is performed prior to or contemporaneously with additively manufacturing the AM object.

14. The method of claim 13, wherein the obtaining of the sample of the raw material is performed within several minutes prior to additively manufacturing the AM object.

15. A system comprising:
an additive manufacturing (AM) printer for printing an AM object, the AM printer including a raw material chamber and a build chamber;
a control system coupled with the AM printer configured to control the printing of the AM object;
a material analysis system coupled with the control system and the AM printer, the control system including object code defining the AM object and the object code includes instructions to the AM printer for manufacturing the AM object, the material analysis system configured to:
obtain a sample of a raw material for manufacturing the AM object from raw material chamber, and
analyze the obtained sample of the raw material to measure a characteristic of the raw material prior to or contemporaneously with additively manufacturing the AM object; and
a conduit directly connecting the raw material chamber with the material analysis system, the conduit configured to provide the obtained sample of the raw material from the raw material chamber to the material analysis system.

16. The system of claim 15, wherein the material analysis system is configured to analyze the obtained sample of the raw material for a defect in the raw material by:
comparing the measured characteristic of the raw material to a threshold characteristic range; and
determine if the measured characteristic deviates from the threshold characteristic range.

17. The system of claim 16, wherein the measured characteristic includes at least one of: a shape of the raw material, a morphology of the raw material, a density of the raw material, a particle size distribution of the raw material, a flow-ability of the raw material, a moisture content of the raw material, or an oxygen pickup of the raw material.

18. The system of claim 15, wherein the material analysis system further comprises:
a sample collector coupled with the conduit for collecting the obtained sample of the raw material from the raw material chamber;
a sieve coupled with the sample collector for straining the obtained sample of the raw material; and
a material analyzer coupled with the sieve for comparing the measured characteristic of the raw material to the threshold characteristic range,
wherein the raw material includes a powder.

19. The system of claim 15, wherein the AM printer further includes an applicator coupled with the raw material chamber, wherein the material analysis system is configured to obtain the sample of the raw material prior to the raw material contacting the applicator to form the AM object.

* * * * *